United States Patent [19]

Gaddy et al.

[11] Patent Number: 5,173,429
[45] Date of Patent: Dec. 22, 1992

[54] *CLOSTRIDIUM LJUNGDAHLII*, AN ANAEROBIC ETHANOL AND ACETATE PRODUCING MICROORGANISM

[75] Inventors: James L. Gaddy; Edgar C. Clausen, both of Fayetteville, Ark.

[73] Assignee: The Board of Trustees of the University of Arkansas, Little Rock, Ark.

[21] Appl. No.: 612,221

[22] Filed: Nov. 9, 1990

[51] Int. Cl.$^5$ .................. C12N 1/20; C12P 7/06; C12N 1/00
[52] U.S. Cl. .................. 435/252.7; 435/161; 435/163; 435/135; 435/842
[58] Field of Search .................. 435/281, 282, 252.7, 435/163, 161, 170, 842

[56] References Cited

U.S. PATENT DOCUMENTS 4,652,526 3/1987 Hsu .

OTHER PUBLICATIONS

Tanner and Gaddy, Amer. Soc. for Microbiology Annual Mtg. 1990 Abstract #R-21, p. 249.
J. Bacteriology, Sep. 1979, Wiegel et al., pp. 800–810, vol. 139, No. 3.
Advanced Studies of Biological Indirect Liquefaction of Coal: Topical Report on Task I: Cultural Identification, Jan. 1989, U.S. Dept. of Energy, Pittsburgh, Energy Technology Center, Contract No. DE-AC2-2-88PC79813.
Vega et al., The Biological Production of Ethanol From Synthesis Gas, Applied Biochemistry and Biotechnology, vol. 20/21, 1989, pp. 781–797.
Barik et al., Biological Production of Alcohols from Coal Through Indirect Liquefaction, The Humana Press, 1988, pp. 363–378.
Klasson et al., Biological Production of Liquid and Gaseous Fuels From Synthesis Gas, Applied Biochemistry and Biotechnology, vol. 24/25, 1990, pp. 1–20.
Lundback et al., Parameters Affecting the Kinetics of Ethanol Production from CO, $CO_2$, and $H_2$ by *Clostridium ljungdahlii*, 12th Symposium on Biotechnology for Fuels and Chemicals, Gatlinburg, Tenn.

*Primary Examiner*—Douglas W. Robinson
*Assistant Examiner*—Jane A. Williams
*Attorney, Agent, or Firm*—Hermann Ivester

[57] ABSTRACT

A newly discovered microorganism was isolated in a biologically pure culture and designated *Clostridium ljungdahlii*, having the identifying characteristics of ATCC No. 49587. Cultured in an aqueous nutrient medium under anaerobic conditions, this microorganism is capable of producing ethanol and acetate from CO and $H_2O$ and/or $CO_2$ and $H_2$ in synthesis gas. Under optimal growth conditions, the microorganism produces acetate in preference to ethanol. Conversely, under non-growth conditions, ethanol production is favored over acetate.

7 Claims, 2 Drawing Sheets

CLOSTRIDIUM LJUNGDAHLII, AN ANAEROBIC ETHANOL AND ACETATE PRODUCING MICROORGANISM

This invention was made with Government support under Contract No. De-AC22-85PC80012 awarded by the Department of Energy.

BACKGROUND OF THE INVENTION

The present invention relates to a biologically pure culture of an anaerobic microorganism and its isolation. More specifically, the present invention relates to the production of ethanol and acetate from carbon monoxide, carbon dioxide, and hydrogen, the major components of synthesis gas.

As a major source of both fuel and chemicals, coal represents the United States' largest fossil energy source. Conversion of coal to a more efficient energy source and a valuable chemical feedstock has been achieved by gasification processes. In most gasification processes, the coal is hydrogasified by adding steam, and energy (20-70 atm), with temperatures reaching as high as 2730° C. Gasification of solid fuels like coal produces synthesis gas, a gas typically consisting of more than 50 percent hydrogen and carbon monoxide. In addition, carbon dioxide is also produced along with small amounts of methane and sulfur gases. Suitable for further processing, synthesis gas can be used as a major intermediate in the production of liquid fuels such as alcohols and petrochemicals.

Recent efforts have focused on developing more efficient and economical methods for using available energy resources. To this end, considerable interest has developed in the biological conversion of synthesis gas components to liquid fuels in view of the distinct advantages offered by microbial processes over traditional catalytic processes.

Chemical conversions require high temperatures and pressures, resulting in losses in thermal efficiency and high energy costs. On the other hand, microbial conversions occur at ambient temperatures and pressures, resulting in substantial energy and equipment savings Also, product yields from microbial conversions are quite high as compared to chemical conversions, since the microorganism utilizes only a small fraction of the substrate for energy and growth. Further, under proper conditions, microbial conversions are quite specific, generally converting a substrate into a single product. It follows that these conversions would have useful application in industrial processes such as chemical feedstock and fuel production.

Conversion of coal to liquid fuels by microorganisms occurs by either direct or indirect biological action. Although direct biological action on coal has tremendous potential, there are several disadvantages exhibited by the processes such as the apparent toxicity of liquefied coal products and waste water streams that result from the coal conversion process.

A more promising biological approach is the indirect coal conversion of synthesis gas by microorganisms capable of producing alcohols and acids from CO, $CO_2$, and $H_2$. A two-step process is required. First, synthesis gas is produced by catalytic action on coal using conventional gasification techniques. The biological conversion of synthesis gas to liquid fuels involves contacting the gas and microorganisms in liquid culture. The gas is then absorbed at the gas-liquid interface and diffuses through the culture medium to the cell surface to be consumed by the microorganisms.

Several species of clostridia have been found to utilize CO and $CO_2/H_2$ as substrates. *Clostridium thermoaceticum* utilizes CO to produce acetate. Similarly, *Clostridium thermoautotrophicum* produces acetate and butyrate from CO, $CO_2$ and $H_2$. Other clostridial species have been shown to ferment $CO_2$ and $H_2$ to formate, acetate, and butyrate. However, no microorganism has, heretofore, been known to form ethanol from synthesis gas components.

SUMMARY OF THE INVENTION

The present invention is directed to the isolation of a biologically pure culture of a newly discovered anaerobic microorganism, *Clostridium ljunqdahlii*. The present invention is further directed to the unique capability of the organism to produce ethanol and acetate from synthesis gas.

In an embodiment of the present invention, the organism produces acetate in preference to ethanol under normal growth conditions, typically between pH 5.0 and 7.0.

In a further embodiment of the present invention, ethanol production is favored over acetate production at pH between 4.0 and 4.5.

In addition, the present invention includes morphological and unique fermentation characteristics that support the scientific conclusion that this microorganism is distinct from previously reported microbiological isolates. Accordingly, an unrestricted deposit of said microorganism was made with the American Type Culture Collection (ATCC), Rockville, Md. on Aug. 17, 1990, under Accession No. 49587.

DETAILED DESCRIPTION OF THE PRESENTLY PREFERRED EMBODIMENTS

Figure 1:
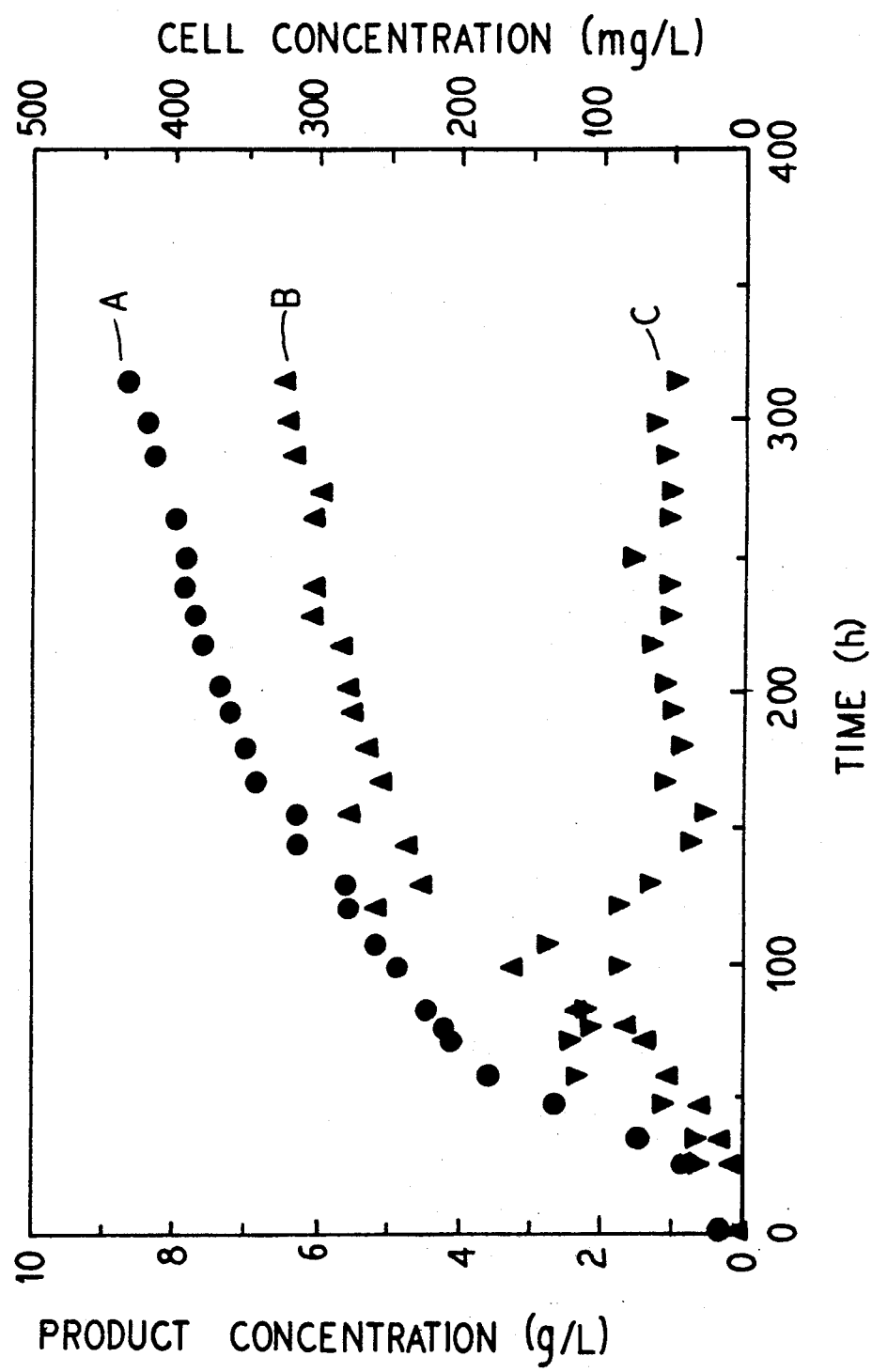
FIG. 1 illustrates the product concentrations (g/L) of ethanol and acetate attained in liquid batch cultures with a continuous gas feed with *Clostridium ljungdahlii*. Plot A represents cell concentration (mg/L) versus time. Plot B represents ethanol concentration (g/L) versus time. Plot C represents acetate concentration versus time.

The present invention describes the isolation of a biologically pure culture of the new anaerobic microorganism, *Clostridium ljungdahlii*, sometimes referred to hereinafter as "*C. ljungdahlii*". Once isolated, biochemical and morphological properties of the organism were analyzed. Although similar to other organisms in its ability to ferment certain carbohydrates, *C. ljungdahlii* is distinguished in its ability to produce ethanol from CO and $H_2O$ and/or $CO_2$ and $H_2$, the major components of synthesis gas. The organism also produces acetate from synthesis gas. In view of its ability to produce ethanol, as discussed in detail below, this organism is deemed a new species designated *Clostridium ljungdahlii*, ATCC No. 49587 being representative of this species.

The microorganism of the present invention was initially isolated from chicken waste. The isolation of *C. ljungdahlii* in a biologically pure form was accomplished using the anaerobic techniques according to Hungate (Bacteriol. Rev. 14: 1–49, 1950), Bryant (Am. J. Clin. Nutr. 25: 1324–1328, 1972), and Balch and Wolfe (Appl. Environ. Microbio. 32: 781–791, 1976), and the methodology of such technique is hereby incorporated in the disclosure by reference.

The medium used for isolation and culture identification studies of the new strain, in accordance with this invention, has the preferred composition as shown in Table 1.

TABLE 1

| Isolation Medium | Per 100 mL of Medium |
| --- | --- |
| Pfennig's minerals | 5.0 mL |
| Pfennig's trace minerals | 0.1 mL |
| B-vitamins | 0.1 mL |
| Yeast extract | 0.1 g |
| Resazurin | 0.5 mL |
| Distilled or deionized water | 100 mL |

Once isolated, the biologically pure culture was maintained in isolation medium (see Table 1) and synthesis gas (65% CO, 24% $H_2$, and 11% $CO_2$). The medium was maintained at a pH of 5.0 and a temperature of 37° C. The culture was stored in a non-shaking incubator (Precision Scientific), and transferred every two weeks.

Extensive studies were subsequently performed to characterize the biochemical properties of the organism. To this end, batch fermentations were initially conducted, as described below, utilizing a variety of substrates.

Media preparation (see Table 1) was carried out in an atmosphere of 80% $N_2$ and 20% $CO_2$, as described by Hungate (Meth. Microb. 3B: 117, 1969) and Lungdahl and Wiegel (Manual of Industrial Microbiology and Biotechnology, American Society for microbiology, pp. 84–96, 1986). The media was anaerobically transferred into serum bottles, sealed, and then autoclaved at 121° C. for 20 minutes. Reducing solutions (cysteine-HCl and sodium sulfide) were added to the serum bottles prior to inoculation with a seed culture. Different substrates were added to the medium. The bottles were placed in a shaker incubator at 37° C. during the experiments. Fermentation products were measured in both the liquid and gas samples that were removed from the serum bottles. Analyses of the alcohol and acid content of the fermentation products were performed by gas chromatography.

To monitor cell viability in each culture, cell concentrations were determined by comparing optical density readings with a standard calibration curve at 580 nm in a Spectronic-20 or Spectronic-21 spectrophotometer (Bausch and Lomb).

Batch fermentations revealed that *C. ljungdahlii* is capable of utilizing various carbon and energy sources (as illustrated in Example 5 and Table 5). Under typical growth conditions (pH 5.0–7.0), it was found that the organism produces significant levels of acetate as compared to ethanol levels when utilizing synthesis gas as a substrate. Preliminary studies show that the organism also produces acetate from a variety of sugar substrates and other carbon sources.

As will be shown in the following examples, a product molar ratio (moles ethanol/moles acetate) of 0.05 and an ethanol concentration of less than 1 g/L was achieved with batch fermentations using a synthesis gas substrate at pH 5.0. By continually optimizing the culture, efforts to improve the product molar ratio in favor of ethanol production were successful. Specifically, it has been found that ethanol production is favored over acetate production under non-growth conditions. For example, by altering the pH and nutrient levels of the organism, ethanol concentrations of approximately 7 g/L and a product ratio of 7 grams ethanol/gram of acetate (9 mols ethanol/mol acetate) were obtained. Improvements were further obtained by utilizing a variety of techniques, including a two-stage continuous contacting (CSTR) system, pH shift, and alternative medium constituents. In a two-stage CSTR, acetate production has been eliminated in the second stage.

By way of example, and not limitation, the following examples serve to further illustrate the present invention in its preferred embodiments.

EXAMPLE 1

Isolation of Clostridium ljungdahlii

Samples from chicken waste were collected under anaerobic conditions. In serum bottles, one ml of sample was added anaerobically to 9 ml of nutrient medium described in Table 1. 0.2 ml of 2.5% $NaS_2$ was added for every 10 ml of solution in order to eliminate any dissolved oxygen. 0.1 ml of either BESA or monensin was added for every 10 ml of solution to block methane production and facilitate alcohol and acid production. It should be noted that all inoculation procedures were performed anaerobically. Further, the medium contained CO (64%, 2 atm) in $CO_2$ and $N_2$ or synthetic synthesis gas (73% CO, 10% $CO_2$, 15% $H_2$, and 2% $CH_4$) as the primary carbon source, although variations in the composition of these gases is acceptable for experimental purposes.

The samples were incubated in a shaking incubator with the pH between 5.0 and 7.0. Once gas consumption had begun, 1.0 ml of the inoculated medium was transferred to new medium. The samples required between 1 and 6 months, but typically 3 months, to initiate gas consumption. The original sample was not discarded. If no gas consumption occurred in the original sample after a period of a month to a month and a half, the sample was transferred to new medium, thus ensuring that the nutrients required for cell growth would not be depleted.

Next, several dilutions were performed in order to purify the culture. The culture was diluted up to $10^{10}$ times with the nutrient medium and then incubated at 37° C. Dilutions of this magnitude helped to ensure the isolation of the most predominant organism. Bacterial growth occurred in all culture tubes up to a dilution of $10^8$ and in some tubes at $10^9$ and $10^{10}$ dilution. Typically, aliquots from the third dilution were spread onto agar plates. However, this step would vary depending upon the density of the cell culture. The plates were then incubated anaerobically at 37° C. The nutrient medium, supplemented with 2% agar, was used for the agar plates. Colonies were isolated from the plates and then inoculated into fresh medium for use in experiments.

A new species of Clostridia was discovered using this technique. This strain was analyzed using conventional microbiological techniques which resulted in characterization and identification as follows:

a. Morphology: Cells grown at 37° C. are rod-shaped and show motility.
b. Spores: Spores are formed infrequently.
c. Other characteristics: The strain is a strict anaerobe and gram-positive.
d. Growth Requirements: The strain requires a minimum level of yeast extract (0.01%) or, in the alternative, an enriched medium containing minerals, trace minerals, B-vitamins, and an amino acid solution. A carbon source is also required.
e. Substrates: The strain ferments a variety of substrates a shown in Example 5 below.
f. Fermentation Products: Under optimal growth conditions (pH 5.0–7.0), the strain ferments synthesis gas to a mixture of ethanol and acetate, producing acetate as the major product and ethanol as the minor product. Under non-growth conditions of pH 4.0–4.5 and without yeast extract as a nutrient source, ethanol is the major product.
g. pH Range: For growth=5.0–7.0.
h. Temperature Optimum (Preliminary)=37° C.

These and other properties described in this invention appear to exclude the new strain from previously identified clostridial species as described in the 8th edition of *Bergey's Manual of Determinative Bacteriology* (Williams and Wilkins Comp. Baltimore) 1974. Therefore, the newly discovered strain represents a new clostridial species that has been named *Clostridium ljungdahlii*, and ATCC No. 49587 is representative of the strain.

EXAMPLE 2

Media Studies

In determining whether media factors influenced alcohol and acid production, studies were performed with *C. ljungdahlii*, utilizing only medium (yeast extract, salts, vitamins). No carbon source such as CO or synthesis gas was added to the medium. Essentially, no alcohol production occurred in the medium at pH 5.0. However, significant levels of organic acids were produced, indicating that the organism was probably using yeast extract as its carbon source.

Experiments were subsequently performed to develop a minimal medium which would sustain growth of and maximize ethanol production by *C. ljungdahlii*. One method involved transferring the organism into medium containing decreasing amounts of yeast extract. Studies indicated that a minimum level of yeast extract (approximately 0.01%) is required as a nutrient source for the organism.

In another method, yeast extract was completely eliminated from the medium. Instead, the enriched medium as shown in Table 2 and an amino acid solution (see Table 3) were utilized. Once the organism adapted to growth in this medium, all solution concentrations were successfully reduced by one-half, except for the trace mineral solution. Further, cell growth was prohibited upon the removal of the B-vitamin solution.

TABLE 2

Enriched Medium Composition/100 mL Medium 5.0 mL mineral solution
0.5 mL trace minerals solution
2.0 mL B-vitamin solution
0.1 mL Resazurin solution (0.1%)

TABLE 2-continued

Enriched Medium Composition/100 mL Medium 80 mL distilled water

| Mineral Solution | g/L | Trace Mineral Solution | (g/L) |
|---|---|---|---|
| $(NH_4)_2SO_4$ | 10.0 | Nitrilotriacetate | 1.5 |
| $NH_4Cl$ | 10.0 | $MgSO_4 \cdot 7H_2O$ | 6.1 |
| $KH_2PO_4$ | 136.0 | NaCl | 1.0 |
| | | $FeSO_4 \cdot 7H_2O$ | 0.1 |
| | | $CoCl_2 \cdot 6H_2O$ | 0.1 |
| | | $CaCl_2 \cdot 2H_2O$ | 0.1 |
| | | $ZnCl_2$ | 0.1 |
| B-vitamins | mg/L | | |
| Biotin | 20 | $CuCl_2 \cdot xH_2O$ | 0.01 |
| Folic Acid | 20 | $AlK(SO_4)_2 \cdot 12H_2O$ | 0.01 |
| Pyridoxal HCl | 10 | $H_3BO_3$ | 0.01 |
| Lipoic A (Thioctica) | 60 | $Na_2MoO_4 \cdot 2H_2O$ | 0.01 |
| Riboflavin | 50 | $NiCl_2 \cdot 6H_2O$ | 0.05 |
| Thiamine HCl | 50 | $Na_2SeO_3$ | 0.0005 |
| Ca-D-Pantothenate | 50 | $MnSO_4 \cdot H_2O$ | 0.5 |
| Cyanocobalamin | 50 | | |
| P-Aminobenzoic Acid | 50 | | |
| Nicotinic Acid | 50 | | |

TABLE 3

Amino Acid Solution Composition (16 mg/L of each)

| | |
|---|---|
| valine | leucine |
| threonine | cysteine |
| arginine | glutamic acid |
| histidine | phenylalanine |
| methionine | serine |
| lysine | asparagine |
| | tryptophan |

EXAMPLE 3

Batch Fermentations

Batch fermentations were conducted using a biologically pure culture of *C. ljungdahlii*. Preparation of the medium (see Table 1) was carried out anaerobically in an atmosphere of 80% nitrogen and 20% $CO_2$. The pH of the medium was controlled during fermentation and maintained at 5.0 with HCl. If required, adjustments to the pH were made with a sterile 10% NaOH or 1.0% acetic acid solution. The medium was transferred to 157.5 ml serum bottles and sealed with butyl rubber stoppers and aluminum seals. The bottles were then autoclaved at 121° C. for 21 minutes.

Approximately 48 hours before commencing the experiment, a seed culture was prepared from a stock culture of the *Clostridium ljungdahlii* in a bottle similar to those as described above. The seed culture was grown in a shaker incubator at 37° C. and shaken at 100 rpm. Reducing solutions (2.0 ml $Na_2S$, 2.5% soln and 2.0 ml cysteine-HCl, 3.5% soln) were added to the culture, which was placed in the shaker incubator for approximately 15 minutes to allow for complete oxygen removal and temperature acclimation. Unlike the procedure used for isolating a biologically pure culture of the organism, addition of methane inhibitors was not required in batch fermentations.

Next, 10 ml of seed culture were aseptically added to serum bottles containing the medium. The bottles were flushed with the gas substrate and pressurized to the desired level (up to 3 atm maximum). Initial partial pressures of synthesis gas ranged from 0.88 to 2.53. 20 ml of methane, an inert gas, was added with a Leur-lock syringe, which allows for changes in total pressure inside the bottles to be determined with high accuracy. The use of either methane or argon as inert gases will not interfere with the organism's ability to produce ethanol and acetate.

During experimentation, the bottles were left in the shaker incubator (100 rpm) at 37° C. Sampling of the gas composition, optical density, pH, and ethanol and acetate concentrations was carried out at appropriate levels. Typically, 0.4 ml gas samples were withdrawn using gas-tight syringes, while 3.0 ml of liquid were anaerobically sampled using syringes.

Gas phase compositions were determined by gas chromatography using a 6 ft. × ⅛ in. Carbosphere, 60/80 mesh column in a two-step temperature program. The gas sample was heated at 30° C. for 4 minutes and then at 125° C. for 5 minutes. A final heating at 200° C. for 8 minutes was required to condition the column prior to analysis of subsequent samples. The detector and injector temperatures were 175° C., and the carrier gas (helium) flow rate was 40 ml/min.

Liquid phase analyses of alcohols and acids were performed by gas chromatography, using a 2 ft. × ⅛ in. column packed with Porapak QS. For alcohol analysis, the column was treated with NaOH. In a typical run, a 250 μl sample was mixed with 40 μl of NaOH to avoid acid peaks. 1 μl samples were injected into the chromatograph. The oven temperature was 150° C., and both the detector and injector temperatures were 220° C. The carrier gas (helium) flow rate was 40 ml/min.

For acid analysis, the column was preconditioned with $H_3PO_4$. Typically, a 250 μl sample was mixed with 40 μl of 50% $H_3PO_4$ and, a 1 μl sample of this mixture was injected into the chromatograph for analysis. The detector and injector were maintained at 220° C., and the oven temperature was set at 170° C. The carrier gas (helium) flow rate was 40 ml/min. Prior to switching from alcohol to acid analysis, it was necessary to change the columns, followed by conditioning overnight at 200° C.

Batch fermentations provided valuable information on the overall performance of the organism. Experiments revealed that *Clostridium ljungdahlii* produces a mixture of ethanol and acetate from CO and $H_2O$ and/or $CO_2$ and $H_2$, the major components of synthesis gas. Under typical growth conditions, the organism produced acetate in preference to ethanol. The product ratio of moles ethanol/moles acetate in batch culture at pH 5.0 was determined to be approximately 0.05, with an ethanol concentration of less than 1 g/L. However, this product ratio appeared to be affected by altering the initial yeast extract concentration in the medium. At lower levels of yeast extract (0.005%, 0.01%, 0.05%), the molar product ratio of ethanol/acetate was approximately 0.11, as compared to a ratio of 0.05 at higher levels of yeast extract (0.1%, 0.2%).

Liquid batch culture experiments with a continuous gas feed were also conducted with *C. ljungdahlii*. As illustrated in FIG. 1, wherein the pH was 4.0 and the yeast extract was completely removed, ethanol concentrations exceeded acetate concentrations. Specifically, with time, the ethanol concentrations reached approximately 7 g/L as compared to acetate concentrations of 1 g/L. These results further demonstrate that greater ethanol production occurs when *C. ljungdahlii* is subjected to non-growth conditions. Conversely, acetate production is favored by conditions that promote cell growth.

Further, the product molar ratios did not appear to be affected by the initial CO or $H_2$ partial pressure used. In batch culture, cell growth was essentially the same at each pressure up to a fermentation time of 100 hours, at which time cell concentrations increased with increasing partial pressure.

EXAMPLE 4

Continuous Fermentation in a CSTR

Efforts to enhance ethanol production and the molar product ratio were successful with the use of a two-stage continuous stirred-tank reactor (CSTR) system. The first reactor in the series was used to promote cell growth, while the second reactor was used to increase ethanol production.

Experiments with *Clostridium ljungdahlii* were performed in two New Brunswick Bioflow C.30 chemostats connected in series. The nutrient medium as described in Table 4 below was fed continuously to Reactor A (first stage) using a Masterflex pump, with gravity overflow of the affluent and cells to Reactor B (second stage). No additional liquid medium was fed to Reactor B. The pH between the reactors was shifted from 5.0 to 4-4.5 to cause the onset of ethanol production while causing growth to cease. Examples of switching of metabolism have been previously reported in the literature. The agitation rate was maintained at 400 rpm in each vessel. The system was maintained at 37° C.

TABLE 4

| Liquid Media Composition | |
|---|---|
| | Per 100 mL of Medium |
| Pfennig's mineral solution | 5.0 mL |
| Pfennig's trace metal solution | 0.1 mL |
| B-vitamins solution | 0.5 mL |
| Resazurin | 0.1 mL |
| Cysteine HCl (2.5% soln) | 2.0 mL |
| Complex nutrient * | |
| Yeast extract | 0.02 g |
| Cellobiose | 0.02 g |
| pH | 5.0 |

* Either yeast extract or cellobiose was used in the studies.

Yeast extract (0.02%) was added to the medium of Reactor A during the first 8 days of the studies. Cellobiose (0.02%) replaced the yeast extract during the last 10 days of the studies.

Each stage was supplied with synthesis gas (55.25% CO, 10.61% $CO_2$, 18.11% $H_2$, and 15.78% Ar [inert]) at identical flow rates. By using a flow breaker between the stages, Reactor B received only overflow liquid from Reactor A, in addition to a fresh gas supply.

Figure 2:
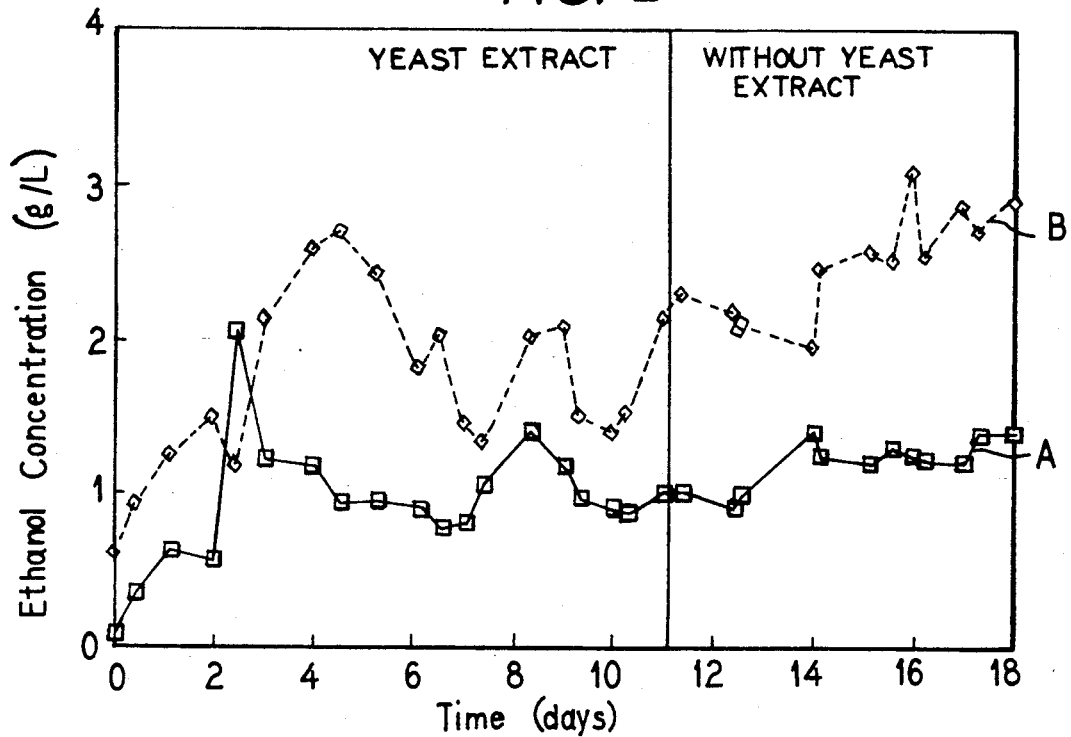
FIG. 2 illustrates ethanol concentrations (g/L) attained in a two-stage CSTR system with *Clostridium ljungdahlii* in the presence of yeast extract and without yeast extract. Plot A represents the first reaction mixture. Plot B represents the second reactor.

As illustrated in FIG. 2, the ethanol concentration in Reactor A increased rapidly during the first 3 days of the studies before stabilizing at 1 g/L. Ethanol concentration increased only slightly to about 1.3 g/L without the use of yeast extract. In Reactor B, the ethanol concentration increased to nearly 3 g/L and appeared to be stimulated by the lack of yeast extract in the medium.

Figure 3:
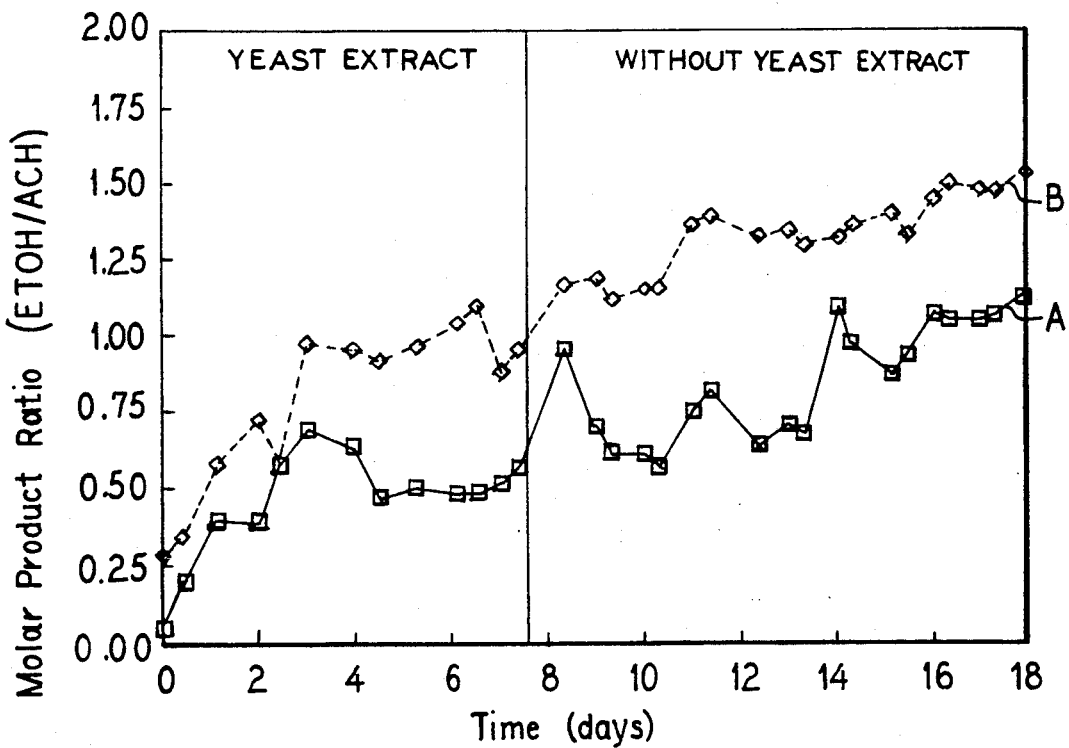
FIG. 3 illustrates the molar product ratio of ethanol/acetate attained in a two-stage CSTR system with *Clostridium ljungdahlii* in the presence of yeast extract and without yeast extract. Plot A refers to the first reactor. Plot B refers to the second reactor.

FIG. 3 illustrates an increase in the molar product ratios (moles ethanol/moles acetate) with time in Reactors A and B. As shown, the molar product ratios reached a maximum of 1.0 in Reactor A and 1.5 in Reactor B. The lack of yeast extract appeared to enhance the product ratio as compared to the ratio in the presence of yeast extract in the medium. A product ratio of 4 moles ethanol/mole of acetate was obtained in Reactor B (second stage) as calculated by subtracting the product concentrations produced in Reactor A from those exiting Reactor B.

Results indicate that the pH shift between the reactors in this system was a significant step in causing *Clostridium ljungdahlii* to shift from acetate production or growth phase to producing ethanol. Further, it appeared that the removal of nutrient sources promotes ethanol production at the expense of acetate production. The substitution of cellobiose indicates that removal of essential nutrients required by the organism to grow results in a shift by the organism from acetate production and a growth phase to ethanol production.

EXAMPLE 5

Fermentations Using Diverse Substrates

Table 5 lists those substrates tested for growth as the sole carbon and energy source for the organism. 1 g/L of yeast extract was added to the medium in addition to the substrate, and all fermentations were conducted at an initial pH of 6.0. As noted in the table, growth occurred when CO, $CO_2/H_2$, ethanol, pyruvate, xylose, arabinose, and fructose were used as substrates. *Clostridium ljungdahlii* grew weakly in the presence of glucose, fumarate, ribose, and casamino acids.

TABLE 5

Growth of *Clostridium ljungdahlii* on Substrates as the Sole Carbon/Energy Source

| | | | |
|---|---|---|---|
| $H_2: CO_2$ | + | ribose | w |
| CO | + | xylose | + |
| formate | − | arabinose | + |
| methanol | − | fructose | + |
| ethanol | + | glucose | w |
| pyruvate | + | galactose | − |
| lactate | − | mannose | − |
| glycerol | − | sorbitol | − |
| succinate | − | sucrose | − |
| fumarate | w | maltose | − |
| citrate | − | lactose | − |
| | | starch | − |

TABLE 5-continued

Growth of *Clostridium ljungdahlii* on Substrates as the Sole Carbon/Energy Source

| | |
|---|---|
| casamino acids | w |

+ positive growth
− no growth
w weak growth

It should be understood that the present invention involves the various embodiments associated with the discovery of *Clostridium ljungdahlii* and its use in all respects, and is not to be construed as limited to any specific aspect or embodiment except as defined by the lawful scope of the appended claims.

We claim:

1. A biologically pure culture of the microorganism *Clostridium ljungdahlii*, having all of the identifying characteristics of ATCC No. 49587.

2. A biologically pure culture of the microorganism *Clostridium ljungdahlii*, having the identifying characteristics of ATCC No. 49587, said culture, under anaerobic conditions, having the ability to produce ethanol and acetate upon fermentation in an aqueous nutrient medium containing synthesis gas as a substrate.

3. The biologically pure culture of claim 2, wherein said substrate is selected from the group consisting essentially of CO, $CO_2$, and $H_2$.

4. A biologically pure culture of the microorganism *Clostridium ljungdahlii*, having all of the identifying characteristics of ATCC No. 49587, said culture, under anaerobic conditions, having the ability to produce acetate in an aqueous nutrient medium comprising sources of carbon.

5. The biologically pure culture of claim 4, wherein said carbon source is a sugar.

6. A biologically pure culture of the microorganism *Clostridium ljungdahlii*, having all of the identifying characteristics of ATCC No. 49587, said culture exhibiting the following characteristics: rod-shaped, motile, gram-positive, and strictly anaerobic.

7. A biologically pure culture of the microorganism *Clostridium ljungdahlii*, having all of the identifying characteristics of ATCC No. 49587, said culture, under anaerobic conditions, having the ability to utilize pyruvate, xylose, arabinose, and fructose as substrates for growth.

* * * * *

UNITED STATES PATENT AND TRADEMARK OFFICE
CERTIFICATE OF CORRECTION

| | |
|---|---|
| PATENT NO. | : 5,173,429 |
| APPLICATION NO. | : 07/612221 |
| DATED | : December 22, 1992 |
| INVENTOR(S) | : James L. Gaddy and Edgar C. Clausen |

It is certified that error appears in the above-identified patent and that said Letters Patent is hereby corrected as shown below:

Title Page item (57)

Abstract, line 4; "No. 49587" should read -- No. 55383 --.

Col. 2, lines 31- 34; "Accordingly, an unrestricted deposit of said microorganism was made with the American Type Culture Collection (ATCC), Rockville, Md. on Aug. 17, 1990 under Accession No. 49587." should read -- Accordingly, unrestricted deposit No. 55383 of said microorganism with the American Type Culture Collection (ATCC), Rockville, Md. is maintained as a transfer of a deposit on Aug. 17, 1990 under Accession No. 49587. --

Col. 3, Line 2; Col. 5, Line 33; "No. 49587" should read -- No. 55383 --

Claims

Col 10, Lines 18, 21, 30, 38, and 43; "No. 49587" should read -- No. 55383 --

Signed and Sealed this

Twentieth Day of March, 2007

JON W. DUDAS
*Director of the United States Patent and Trademark Office*